United States Patent
Smith et al.

(10) Patent No.: US 10,717,694 B2
(45) Date of Patent: Jul. 21, 2020

(54) HYDROFLUOROOLEFINS AND METHODS OF USING SAME

(71) Applicant: 3M INNOVATIVE PROPERTIES COMPANY, St. Paul, MN (US)

(72) Inventors: Sean M. Smith, Woodbury, MN (US); William M. Lamanna, Stillwater, MN (US); Michael G. Costello, Afton, MN (US); Michael J. Bulinski, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/099,719

(22) PCT Filed: May 1, 2017

(86) PCT No.: PCT/IB2017/052525
§ 371 (c)(1),
(2) Date: Nov. 8, 2018

(87) PCT Pub. No.: WO2017/195070
PCT Pub. Date: Nov. 16, 2017

(65) Prior Publication Data
US 2019/0185402 A1 Jun. 20, 2019

Related U.S. Application Data

(60) Provisional application No. 62/333,330, filed on May 9, 2016.

(51) Int. Cl.
| | |
|---|---|
| *C09K 5/00* | (2006.01) |
| *C07C 43/17* | (2006.01) |
| *C09K 5/10* | (2006.01) |
| *C09K 5/04* | (2006.01) |
| *C07C 43/16* | (2006.01) |

(52) U.S. Cl.
CPC ............ *C07C 43/17* (2013.01); *C09K 5/04* (2013.01); *C09K 5/045* (2013.01); *C09K 5/10* (2013.01); *C07C 43/16* (2013.01); *C09K 2205/112* (2013.01); *C09K 2205/126* (2013.01)

(58) Field of Classification Search
CPC .......... C07C 43/17; C07C 43/16; C09K 5/00; C09K 5/04; C09K 5/044; C09K 5/045; C09K 2205/112; C09K 2205/126
USPC ........................................................ 252/78
See application file for complete search history.

(56) References Cited

U.S. PATENT DOCUMENTS

| | | | |
|---|---|---|---|
| 3,114,778 A | 12/1963 | Fritz | |
| 4,788,352 A * | 11/1988 | Smutny | C07C 17/275 570/136 |
| 6,203,944 B1 | 3/2001 | Turner | |
| 6,303,080 B1 | 10/2001 | Tuma | |
| 6,908,724 B2 | 6/2005 | Araki | |
| 7,566,409 B1 | 7/2009 | Zastrow | |
| 10,266,472 B2 * | 4/2019 | Bulinski | C08F 16/24 |
| 10,308,592 B2 * | 6/2019 | Lamanna | C08J 9/14 |
| 10,577,335 B2 * | 3/2020 | Smith | C10L 1/224 |
| 2001/0024701 A1 * | 9/2001 | Matsukura | G03F 1/62 428/14 |
| 2004/0142286 A1 * | 7/2004 | French | G03F 1/62 430/320 |
| 2007/0069175 A1 | 3/2007 | Thomas | |
| 2008/0227948 A1 | 9/2008 | Tsuda | |
| 2009/0183856 A1 * | 7/2009 | Bulinski | C09K 5/10 165/80.4 |
| 2010/0025619 A1 * | 2/2010 | Riva | C09K 5/045 252/67 |
| 2010/0139274 A1 | 6/2010 | Zyhowski | |
| 2011/0021716 A1 | 1/2011 | Wasino | |
| 2011/0010060 A1 | 5/2011 | Flynn | |

(Continued)

FOREIGN PATENT DOCUMENTS

| | | |
|---|---|---|
| CN | 103840178 | 6/2014 |
| FR | 1362548 | 6/1964 |

(Continued)

OTHER PUBLICATIONS

Bardin, "The reactivity of potassium polyfluoroalkenyl-, and Perfluoroalkyltrifluoroborates and their Hydrocarbon Analogues towards Acids of Different Stregth: A systematic study of the hydrodeboration", Z.Anorg.Allg.Chem., 2002, vol. 628, pp. 883-890.

Barlow, "The effect of substituents on $J_{vic}^{FF}$ IN 1,2-difloroethylenes", Chemical Communications, 1966, No. 19, pp. 703-704.

Brandwood, "Polyfluoro diethyl and ethyl methyl ethers: The preparation using cobalt (III) fluoride and potassium tetrafluor ocoboltate(III) and their dehydrofluorination", Journal of Fluorine Chemistry, 1975, No. 5, pp. 521-535.

(Continued)

*Primary Examiner* — Jane L Stanley
(74) *Attorney, Agent, or Firm* — Adam Bramwell

(57) ABSTRACT

A hydrofluoroolefin compound is represented by the following general formula (I): where $R_f$ is a linear or branched perfluorinated alkyl group containing 2-10 carbon atoms and optionally contains (i) at least one catenated heteroatom selected from O or N; or (ii) a ring structure having 3 to 6 ring carbon atoms that optionally contains one or more catentated heteroatoms selected from O or N.

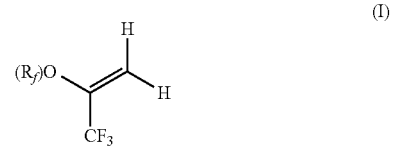

(I)

10 Claims, No Drawings

(56) References Cited

U.S. PATENT DOCUMENTS

| | | | |
|---|---|---|---|
| 2011/0100601 A1* | 5/2011 | Flynn | C09K 5/10 165/104.19 |
| 2012/0006510 A1* | 1/2012 | Bartelt | C09K 5/10 165/104.11 |
| 2013/0091843 A1* | 4/2013 | Zyhowski | C07C 21/18 60/651 |
| 2013/0109797 A1 | 5/2013 | Fantoni | |
| 2013/0261249 A1 | 10/2013 | Apostolo | |
| 2013/0267618 A1 | 10/2013 | Colaianna | |
| 2018/0141893 A1* | 5/2018 | Lamanna | C07C 211/24 |
| 2019/0337933 A1* | 11/2019 | Bulinski | C07D 413/06 |

FOREIGN PATENT DOCUMENTS

| | | |
|---|---|---|
| JP | 2008-116843 | 5/2008 |
| JP | 2009-006586 | 1/2009 |
| JP | 2009-116843 | 5/2009 |
| JP | 2009-186786 | 8/2009 |
| JP | 2013-045728 | 3/2013 |
| RU | 2407753 | 12/2010 |
| WO | WO 2000-003444 | 1/2000 |
| WO | WO 2004-060849 | 7/2004 |
| WO | WO 2008/006866 | 1/2008 |
| WO | WO 2008-070606 | 6/2008 |
| WO | WO 2009-123013 | 10/2009 |
| WO | WO 2015-028761 | 3/2015 |
| WO | WO 2016-011220 | 1/2016 |

OTHER PUBLICATIONS

Coe, "Chloropolyfluoro-derivatives of ethyl methyl ether", Journal of fluorine chemistry, 1997, vol. 82, pp. 09-12.

Coe, "Fluorinations with Potassium Tetrafluorocobaltate(III). Part VI. Fluorination of Pyridine and 4-Methylpyridine" J. Chem. Soc. Perkin 1, Organic and Bioorganic Chemistry, 1974, pp. 1732-1736.

Coe, "Highly fluorinated heterocycles—XI[1] The preparation of some polyfluoro-p-dioxenes: Some reactions of hexafluoro-p-dioxene", Journal of Fluorine Chemistry, 1975, No. 6, pp. 115-128.

Dlouha, "Reactivity study of 1,1,2,4,4,5,7,7,8,8,9,9,9-tridecafluoro-5-trifluoromethyl-3, 6-dioxanon-1-ene in nucleophilic reactions: fluorination properties of secondary amine adducts", Journal of Fluorine Chemistry, 2002, vol. 117, pp. 149-159.

Ellis, "Cleaning and flux removal using organic solvents", Electrochemical Publications Limited, 1986, Scotland, pp. 182-194.

Fleming, "Polyfluoroalkyl derivatives of nitrogen. Part XXX. Reaction of N-Chlorobistrufluoromethylamine with propene and vinyl fluoride and of N-Iodobistrifluoromethylamine with Vinyl fluoride under ionic conditions", J. Chem. Soc. (C), 1971, pp. 3829-3833.

Fleming, "Polyfluoroalkyl Derivatives of Nitrogen. Part XXXVI. Photochemical Reaction of N-Bromo- and N-Chloro-bistrifluoromethylamine with cis- of trans-But-2-ene, and the Synthesis of 1,2-Di(bistrifluromethylamino)-difluoroethylene and 2-Bromo-1,2-difluoro-nn-bistrifluoromethylvinylamine", J. Chem. Soc. Perkin. 1: Organic and Bio-Organic Chemistry, 1972, No. 15, pp. 1877-1879.

Frohn, "The unusual reactivity of $C_3F_7OCF=CF_2$ with $PBu_3$ and the complex hydrides $M[EH_4]$ (M: Li, Na; E: B, Al); preparation of potassium perfluoro-2-propoxyeth-1-enyltrifluoroborate $K[C_3F_7OCF=CFBF_3]$", Journal of Fluorine Chemistry, 2003, vol. 123, pp. 43-49.

Haszeldine, "Perfluoroalkyl derivatives of nitrogen. Part XXVI. The preparation and rearrangement of polyuorovinylamines and of trifluoromethyl trifluorovinyl ether", J. Chem. Soc. [Section] C, 1968, No. 4, 398-405.

Russell, "Laser pyrolysis studies of B-diketonate chemical vapour deposition precursors. Part 1: B-diketones", 2005, vol. 29, pp. 485-492.

International Search report for PCT International Application No. PCT/IB17/52525 dated Aug. 16, 2017, 2 pages.

Extended EP Search Report, EP17795699.2, dated Nov. 7, 2019 (5 pages).

* cited by examiner

HYDROFLUOROOLEFINS AND METHODS OF USING SAME

Cross Reference to Related Applications

This application is a national stage filing under 35 U.S.C. 371 of PCT/IB2017/052525, filed May 1, 2017, which claims the benefit of U.S. Provisional Application No. 62/333,330, filed May 9, 2016, the disclosure of which is incorporated by reference in its entirety herein.

FIELD

The present disclosure relates to hydrofluoroolefins and methods of making and using the same, and to working fluids that include the same.

BACKGROUND

Various hydrofluoroolefin compounds are described in, for example, Paul L. Coe, et. al., J. Chem. Soc. Perkin Trans. 1, Organic and Bioorganic Chemistry, 1974, 1732-1736; A. E. Tipping, et. al., J. Chem. Soc. [Section] C: Organic (1971), (22), 3289; M. G. Barlow, Chem. Commun, (1966), (19), 703; A. E. Tipping et. al., J. Chem. Soc. Perkin Trans. 1: Organic and Bio-Organic Chemistry (1972), (15), 1877; and A. E. Tipping, et. al., J. Chem. Soc. [Section] C: Organic (1968), (4), 398.

SUMMARY

In some embodiments, a hydrofluoroolefin compound is provided. The hydrofluoroolefin compound is represented by the following general formula (I):

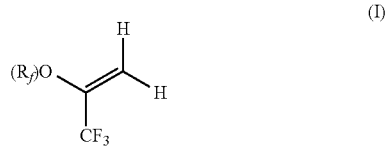

(I)

where $R_f$ is a linear or branched perfluorinated alkyl group containing 2-10 carbon atoms and optionally contains (i) at least one catenated heteroatom selected from O or N; or (ii) a ring structure having 3 to 6 ring carbon atoms that optionally contains one or more catentated heteroatoms selected from O or N.

In some embodiments, a working fluid is provided. The working fluid includes the above-described hydrofluoroolefin compound. The above-described hydrofluoolefin compound is present in the working fluid at an amount of at least 25% by weight, based on the total weight of the working fluid.

In some embodiments, an apparatus for heat transfer is provided. The apparatus includes a device and a mechanism for transferring heat to or from the device. The mechanism for transferring heat includes a heat transfer fluid that includes the above-described hydrofluoolefin compound or working fluid.

In some embodiments, a method of transferring heat is provided. The method includes providing a device and transferring heat to or from the device using a heat transfer fluid that includes the above-described hydrofluoroolefin compound or working fluid.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

In view of an increasing demand for environmentally friendly and low toxicity chemical compounds, it is recognized that there exists an ongoing need for new working fluids that provide further reductions in environmental impact and toxicity, and which can meet the performance requirements (e.g., nonflammability, solvency, stability, and operating temperature range) of a variety of different applications (e.g., heat transfer, solvent cleaning, deposition coating solvents, and electrolyte solvents and additives), and be manufactured cost-effectively. Currently, the materials used in these applications are fluorinated fluids, such as hydrofluoroethers (HFEs), hydrofluorocarbons (HFCs), perfluorocarbons (PFCs), and hydrochlorofluorocarbons (HCFCs).

Generally, the present disclosure provides a new class of fluorinated compounds useful as working fluids. The new fluorinated compounds are oxygen-containing hydrofluoroolefins (HFOs), which provide similar physical properties to existing fluorinated fluids, but generally provide lower atmospheric lifetimes and global warming potentials to provide a more acceptable environmental profile.

As used herein, "catenated heteroatom" means an atom other than carbon (for example, oxygen, nitrogen, or sulfur) that is bonded to at least two carbon atoms in a carbon chain (linear or branched or within a ring) so as to form a carbon-heteroatom-carbon linkage.

As used herein, "fluoro-" (for example, in reference to a group or moiety, such as in the case of "fluoroalkylene" or "fluoroalkyl" or "fluorocarbon") or "fluorinated" means (i) partially fluorinated such that there is at least one carbon-bonded hydrogen atom, or (ii) perfluorinated.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to hydrofluoroolefin compounds represented by the following general formula (I):

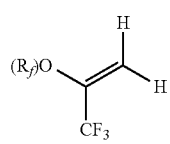
(I)

wherein $R_f$ is a linear or branched perfluorinated alkyl group containing 2-10, 3-10, or 4-10 carbon atoms and optionally includes (i) at least one catenated heteroatom selected from O or N; or (ii) a ring structure having 3 to 6 ring carbon atoms that optionally includes one or more catenated heteroatoms selected from O or N. In some embodiments, $R_f$ is linear. In some embodiments, $R_f$ is branched.

In some embodiments, any of the above discussed catentated heteroatoms may be secondary O heteroatoms wherein the O is bonded to two carbon atoms. In some embodiments, any of the above discussed catenated heteroatoms may be tertiary N heteroatoms wherein the N is bonded to three perfluorinated carbon atoms.

In some embodiments, the fluorine content in the hydrofluoroolefin compounds of the present disclosure may be sufficient to make the compounds non-flammable according to ASTM D-3278-96 e-1 test method ("Flash Point of Liquids by Small Scale Closed Cup Apparatus").

In various embodiments, representative examples of the compounds of general formula (I) include the following:

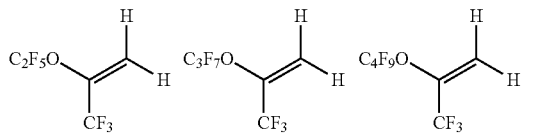

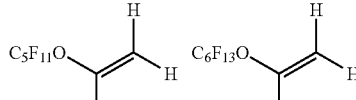

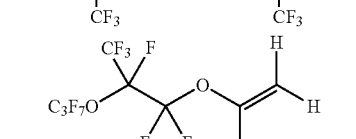

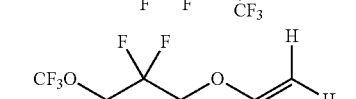

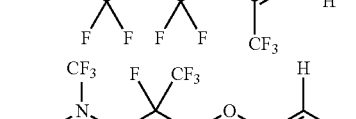

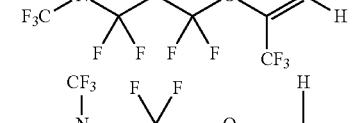

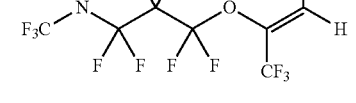

-continued

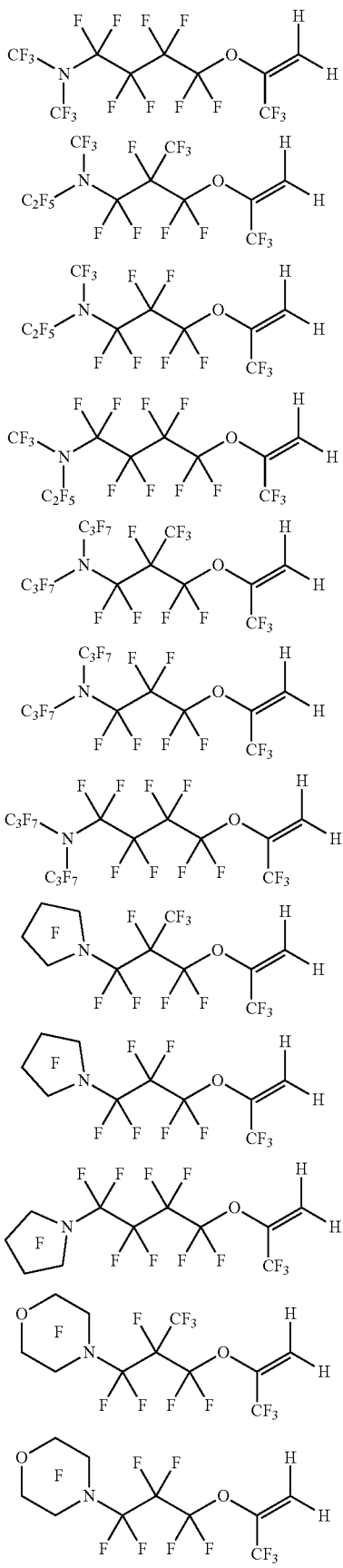

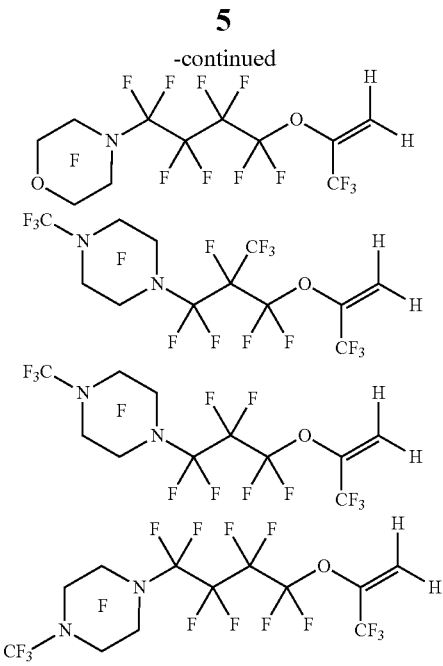

In some embodiments, the hydrofluoroolefin compounds of the present disclosure may be hydrophobic, relatively chemically unreactive, and thermally stable. The hydrofluoroolefin compounds may have a low environmental impact. In this regard, the hydrofluoroolefin compounds of the present disclosure may have a global warming potential (GWP) of less than 500, 300, 200, 100 or less than 10. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, τ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the hydrofluoroolefin compounds represented by general formula (I) can be synthesized using perfluorinated acid fluoride starting materials having the following general formula II:

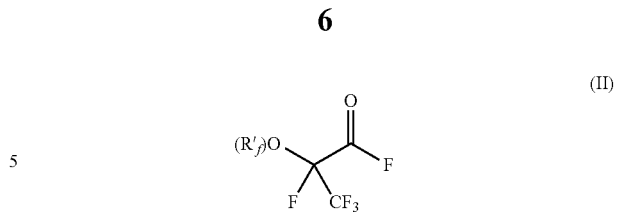

where R'$_f$ is a linear or branched perfluorintated alkyl group containing 2-10, 3-10, or 4-10 carbon atoms and optionally includes (i) at least one catenated heteroatom selected from O or N; or (ii) a ring structure having 3 to 6 ring carbon atoms that optionally includes one or more catentated heteroatoms selected from O or N. In various embodiments, representative examples of the compounds of general formula (II) include the following:

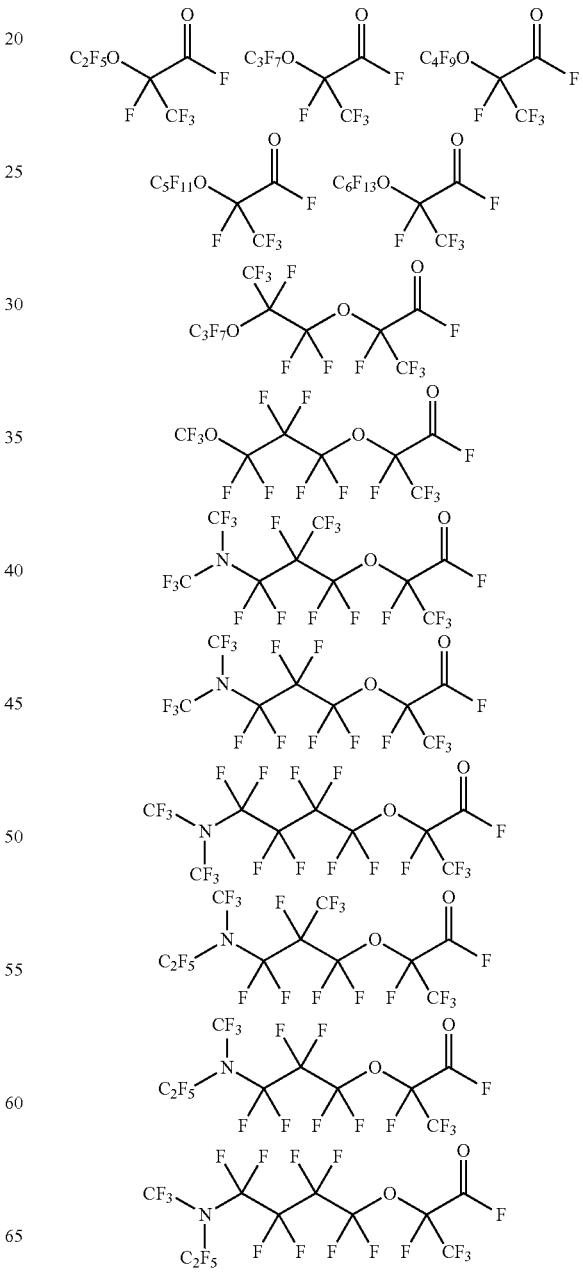

-continued

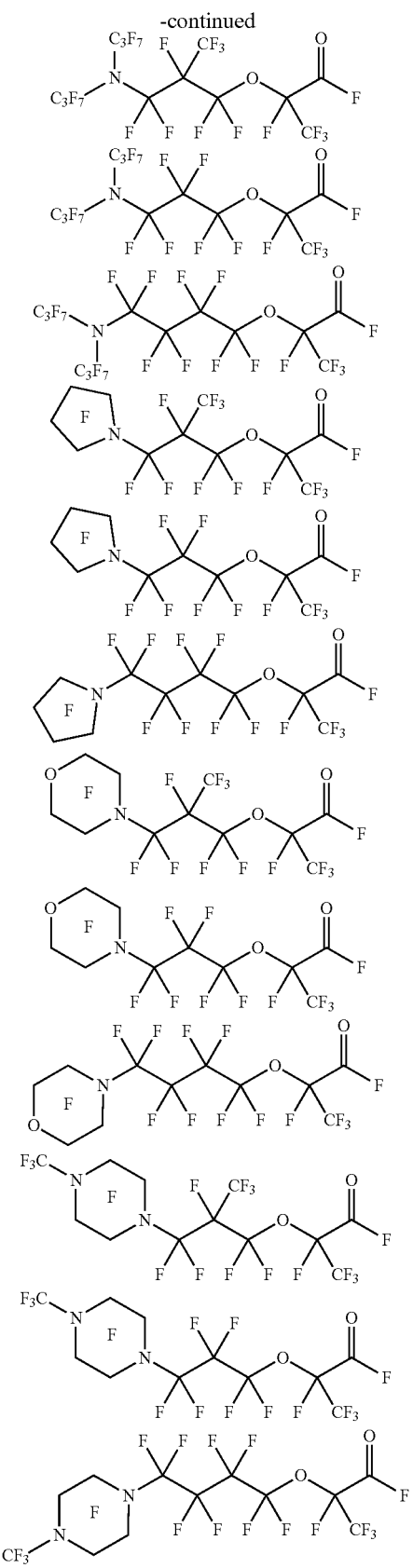

In some embodiments, the hydrofluoroolefin compounds represented by general formula (I) can be synthesized from the aforementioned perfluorinated acid fluorides using the synthetic procedures discussed in International Publication WO 2008/070606 or U.S. Pat. No. 3,114,778, which are both hereby incorporated by reference in their entireties. Alternatively, the hydrofluoroolefin compounds represented by general formula (I) can be synthesized from the aforementioned perfluorinated acid fluorides using any other relevant conventional synthetic procedures.

In some embodiments, the present disclosure is further directed to working fluids that include the above-described hydrofluoroolefin compounds as a major component. For example, the working fluids may include at least 25%, at least 50%, at least 70%, at least 80%, at least 90%, at least 95%, or at least 99% by weight of the above-described hydrofluoroolefin compounds based on the total weight of the working fluid. In addition to the hydrofluoroolefin compounds, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof, based on the total weight of the working fluid. Such additional components can be chosen to modify or enhance the properties of a composition for a particular use.

In some embodiments, the present disclosure is further directed to an apparatus for heat transfer that includes a device and a mechanism for transferring heat to or from the device. The mechanism for transferring heat may include a heat transfer working fluid that includes a hydrofluoroolefin compounds of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, heat exchangers, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more hydrofluoroolefin compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In some embodiments, the present disclosure is directed to a fire extinguishing composition. The composition may include one or more hydrofluoroolefin compounds of the present disclosure and one or more co-extinguishing agents.

In illustrative embodiments, the co-extinguishing agent may include hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, hydrobromocarbons, iodofluorocarbons, fluorinated ketones, hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, unsaturated fluoro-ethers, bromofluoroolefins, chlorofluoroolefins, iodofluoroolefins, fluorinated vinyl amines, fluorinated aminopropenes and mixtures thereof.

Such co-extinguishing agents can be chosen to enhance the extinguishing capabilities or modify the physical properties (e.g., modify the rate of introduction by serving as a propellant) of an extinguishing composition for a particular type (or size or location) of fire and can preferably be utilized in ratios (of co-extinguishing agent to hydrofluoroolefin compound) such that the resulting composition does not form flammable mixtures in air.

In some embodiments, the hydrofluoroolefin compounds and the co-extinguishing agent may be present in the fire extinguishing composition in amounts sufficient to suppress or extinguish a fire. The hydrofluoroolefin compounds and the co-extinguishing agent can be in a weight ratio of from about 9:1 to about 1:9.

In some embodiments, the present disclosure is directed to an apparatus for converting thermal energy into mechanical energy in a Rankine cycle. The apparatus may include a working fluid that includes one or more hydrofluoroolefin compounds of the present disclosure. The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more hydrofluoroolefin compounds of the present disclosure to form a vaporized working fluid. In some embodiments, the heat is transferred from the heat source to the working fluid in an evaporator or boiler. The vaporized working fluid may pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.). The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

In some embodiments, the present disclosure relates to the use of the hydrofluoroolefin compounds of the present disclosure as nucleating agents in the production of polymeric foams and in particular in the production of polyurethane foams and phenolic foams. In this regard, in some embodiments, the present disclosure is directed to a foamable composition that includes one or more blowing agents, one or more foamable polymers or precursor compositions thereof, and one or more nucleating agents that include a hydrofluoroolefin compound of the present disclosure.

In some embodiments, a variety of blowing agents may be used in the provided foamable compositions including liquid or gaseous blowing agents that are vaporized in order to foam the polymer or gaseous blowing agents that are generated in situ in order to foam the polymer. Illustrative examples of blowing agents include hydrochlorofluorocarbons (HCFCs), hydrofluorocarbons (HFCs), hydrochlorocarbons (HCCs), iodofluorocarbons (IFCs), hydrocarbons, hydrofluoroolefins (HFOs) and hydrofluoroethers (HFEs). The blowing agent for use in the provided foamable compositions can have a boiling point of from about −45° C. to about 100° C. at atmospheric pressure. Typically, at atmospheric pressure the blowing agent has a boiling point of at least about 15° C., more typically between about 20° C. and about 80° C. The blowing agent can have a boiling point of between about 30° C. and about 65° C. Further illustrative examples of blowing agents that can be used include aliphatic and cycloaliphatic hydrocarbons having about 5 to about 7 carbon atoms, such as n-pentane and cyclopentane, esters such as methyl formate, HFCs such as $CF_3CF_2CHFCHFCF_3$, $CF_3CH_2CF_2H$, $CF_3CH_2CF_2CH_3$, $CF_3CF_2H$, $CH_3CF_2H$ (HFC-152a), $CF_3CH_2CH_2CF_3$ and $CHF_2CF_2CH_2F$, HCFCs such as $CH_3CCl_2F$, $CF_3CHCl_2$, and $CF_2HCl$, HCCs such as 2-chloropropane, and IFCs such as $CF_3I$, and HFEs such as $C_4F_9OCH_3$ and HFOs such as $CF_3CH=CH_2$, $CF_3CH=CHF$, $CF_3CH=CHCl$ and $CF_3CH=CHCF_3$. In certain formulations $CO_2$ generated from the reaction of water with foam precursor such as an isocyanate can be used as a blowing agent.

In various embodiments, the provided foamable composition may also include one or more foamable polymers or a precursor composition thereof. Foamable polymers suitable for use in the provided foamable compositions include, for example, polyolefins, e.g., polystyrene, poly(vinyl chloride), and polyethylene. Foams can be prepared from styrene polymers using conventional extrusion methods. The blowing agent composition can be injected into a heat-plastified styrene polymer stream within an extruder and admixed therewith prior to extrusion to form foam. Representative examples of suitable styrene polymers include, for example, the solid homopolymers of styrene, α-methylstyrene, ring-alkylated styrenes, and ring-halogenated styrenes, as well as copolymers of these monomers with minor amounts of other readily copolymerizable olefinic monomers, e.g., methyl methacrylate, acrylonitrile, maleic anhydride, citraconic anhydride, itaconic anhydride, acrylic acid, N-vinylcarbazole, butadiene, and divinylbenzene. Suitable vinyl chloride polymers include, for example, vinyl chloride homopolymer and copolymers of vinyl chloride with other vinyl monomers. Ethylene homopolymers and copolymers of ethylene with, e.g., 2-butene, acrylic acid, propylene, or butadiene may also be useful. Mixtures of different types of polymers can be employed.

In various embodiments, the foamable compositions of the present disclosure may have a molar ratio of nucleating agent to blowing agent of no more than 1:50, 1:25, 1:9, or 1:7, 1:3, or 1:2.

Other conventional components of foam formulations can, optionally, be present in the foamable compositions of the present disclosure. For example, cross-linking or chain-extending agents, foam-stabilizing agents or surfactants, catalysts and fire-retardants can be utilized. Other possible components include fillers (e.g., carbon black), colorants, fungicides, bactericides, antioxidants, reinforcing agents, antistatic agents, and other additives or processing aids.

In some embodiments, polymeric foams can be prepared by vaporizing at least one liquid or gaseous blowing agent or generating at least one gaseous blowing agent in the presence of at least one foamable polymer or a precursor composition thereof and a nucleating agent as described above. In further embodiments, polymeric foams can be prepared using the provided foamable compositions by vaporizing (e.g., by utilizing the heat of precursor reaction) at least one blowing agent in the presence of a nucleating agent as described above, at least one organic polyisocyanate and at least one compound containing at least two reactive hydrogen atoms. In making a polyisocyanate-based foam, the polyisocyanate, reactive hydrogen-containing compound, and blowing agent composition can generally be combined, thoroughly mixed (using, e.g., any of the various known types of mixing head and spray apparatus), and permitted to expand and cure into a cellular polymer. It is often convenient, but not necessary, to preblend certain of the components of the foamable composition prior to reaction of the polyisocyanate and the reactive hydrogen-containing compound. For example, it is often useful to first blend the reactive hydrogen-containing compound, blowing agent composition, and any other components (e.g., surfactant) except the polyisocyanate, and to then combine the resulting mixture with the polyisocyanate. Alternatively, all components of the foamable composition can be introduced separately. It is also possible to pre-react all or a portion of the reactive hydrogen-containing compound with the polyisocyanate to form a prepolymer.

In some embodiments, the present disclosure is directed to dielectric fluids that include one or more hydrofluoroolefin compounds of the present disclosure, as well as to electrical devices (e.g., capacitors, switchgear, transformers, or electric cables or buses) that include such dielectric fluids. For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more hydrofluoroolefin compounds of the present disclosure and, optionally, one or more second dielectric fluids. Suitable second dielectric fluids include, for example, air, nitrogen, helium, argon, and carbon dioxide, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application are useful for electrical insulation and for arc quenching and current interruption equipment used in the transmission and distribution of electrical energy. Generally, there are three major types of electrical devices in which the fluids of the present disclosure can be used: (1) gas-insulated circuit breakers and current-interruption equipment, (2) gas-insulated transmission lines, and (3) gas-insulated transformers. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

In some embodiments, the present disclosure relates to coating compositions that include a solvent composition that one or more hydrofluoroolefin compounds of the present disclosure, and one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof.

For example, coating materials may include perfluoropolyether, hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the hydrofluoroolefin compounds function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more of the hydrofluoroolefin compounds; and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the hydrofluoroolefin compound(s), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure relates to cleaning compositions that include one or more hydrofluoroolefin compounds of the present disclosure, and one or more co-solvents.

In some embodiments, the hydrofluoroolefin compounds may be present in an amount greater than 50 weight percent, greater than 60 weight percent, greater than 70 weight percent, or greater than 80 weight percent based upon the total weight of the hydrofluoroolefin compounds and the co-solvent(s).

In various embodiments, the cleaning composition may further comprise a surfactant. Suitable surfactants include those surfactants that are sufficiently soluble in the fluorinated olefin, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylatedalkyl phenols, ethoxylated fatty acids, alkylarysulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble oil removal. The surfactant, if used, can be added in an amount sufficient to promote soil removal. Typically, surfactant is added in amounts from about 0.1 to 5.0 wt. %, preferably in amounts from about 0.2 to 2.0 wt. % of the cleaning composition.

In illustrative embodiments, the co-solvent may include alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof. Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof.

In some embodiments, the present disclosure relates to a process for cleaning a substrate. The cleaning process can be carried out by contacting a contaminated substrate with a cleaning composition as discussed above. The hydrofluoroolefin compounds can be utilized alone or in admixture with each other or with other commonly-used cleaning solvents, e.g., alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof. Such co-solvents can be chosen to modify or enhance the solvency properties of a cleaning composition for a particular use and can be utilized in ratios (of co-solvent to hydrofluoroolefin compounds) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more hydrofluoroolefin compounds of the present disclosure and optionally one or more surfactants. Suitable surfactants include those surfactants that are sufficiently soluble in the hydrofluoroolefin compounds, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning processes of the disclosure can also be used to dissolve or remove most contaminants from the surface of a substrate. For example, materials such as light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; water; and other contaminants encountered in precision, electronic, metal, and medical device cleaning can be removed.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In some embodiments, the present disclosure further relates to electrolyte compositions that include one or more hydrofluoroolefin compounds of the present disclosure. The electrolyte compositions may comprise (a) a solvent composition including one or more of the hydrofluoroolefin compounds; and (b) at least one electrolyte salt. The electrolyte compositions of the present disclosure exhibit excellent oxidative stability, and when used in high voltage electrochemical cells (such as rechargeable lithium ion batteries) provide outstanding cycle life and calendar life. For example, when such electrolyte compositions are used in an electrochemical cell with a graphitized carbon electrode, the electrolytes provide stable cycling to a maximum charge voltage of at least 4.5V and up to 6.0V vs. Li/Li$^+$.

Electrolyte salts that are suitable for use in preparing the electrolyte compositions of the present disclosure include those salts that comprise at least one cation and at least one weakly coordinating anion (the conjugate acid of the anion having an acidity greater than or equal to that of a hydrocarbon sulfonic acid (for example, a bis(perfluoroalkanesulfonyl)imide anion); that are at least partially soluble in a selected hydrofluoroolefin compound (or in a blend thereof with one or more other hydrofluoroolefin compounds or one or more conventional electrolyte solvents); and that at least partially dissociate to form a conductive electrolyte composition. The salts may be stable over a range of operating voltages, are non-corrosive, and are thermally and hydrolytically stable. Suitable cations include alkali metal, alkaline earth metal, Group BIB metal, Group IIIB metal, transition metal, rare earth metal, and ammonium (for example, tetraalkylammonium or trialkylammonium) cations, as well as a proton. In some embodiments, cations for battery use include alkali metal and alkaline earth metal cations. Suitable anions include fluorine-containing inorganic anions such as $(FSO_2)_2N^-$, $BF_4^-$, $PF_6^-$, $AsF_6^-$, and $SbF_6^-$; $ClO_4^-$; $HSO_4^-$, $H_2PO_4^-$; organic anions such as alkane, aryl, and alkaryl sulfonates; fluorine-containing and nonfluorinated tetraarylborates; carboranes and halogen-, alkyl-, or haloalkylsubstituted carborane anions including metallocarborane anions; and fluorine-containing organic anions such as perfluoroalkanesulfonates, cyanoperfluoroalkanesulfonylamides, bis(cyano)perfluoroalkanesulfonylmethides, bis(perfluoroalkanesulfonyl)imides, bis(perfluoroalkanesulfonyl)methides, and tris(perfluoroalkanesulfonyl)methides; and the like. Preferred anions for battery use include fluorine-containing inorganic anions (for example, $(FSO_2)_2N^-$, $BF_4^-$, $PF_6^-$, and $AsF_6^-$) and fluorine-containing organic anions (for example, perfluoroalkanesulfonates, bis(perfluoroalkanesulfonyl)imides, and tris(perfluoroalkanesulfonyl)methides). The fluorine-containing organic anions can be either fully fluorinated, that is perfluorinated, or partially fluorinated (within the organic portion thereof). In some embodiments, the fluorine-containing organic anion is at least about 80 percent fluorinated (that is, at least about 80 percent of the carbon-bonded substituents of the anion are fluorine atoms). In some embodiments, the anion is perfluorinated (that is, fully fluorinated, where all of the carbon-bonded substituents are fluorine atoms). The anions, including the perfluorinated anions, can contain one or more catenary heteroatoms such as, for example, nitrogen, oxygen, or sulfur. In some embodiments, fluorine-containing organic anions include perfluoroalkanesulfonates, bis(perfluoroalkanesulfonyl)imides, and tris(perfluoroalkanesulfonyl)methides.

In some embodiments, the electrolyte salts may include lithium salts. Suitable lithium salts include, for example, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(fluorosulfonyl)imide (Li-FSI), and mixtures of two or more thereof.

The electrolyte compositions of the present disclosure can be prepared by combining at least one electrolyte salt and a solvent composition including at least one hydrofluoroolefin compound of the present disclosure, such that the salt is at least partially dissolved in the solvent composition at the desired operating temperature. The hydrofluoroolefin compounds (or a normally liquid composition including, consisting, or consisting essentially thereof) can be used in such preparation.

In some embodiments, the electrolyte salt is employed in the electrolyte composition at a concentration such that the conductivity of the electrolyte composition is at or near its maximum value (typically, for example, at a Li molar concentration of around 0.1-4.0 M, or 1.0-2.0 M, for electrolytes for lithium batteries), although a wide range of other concentrations may also be employed.

In some embodiments, one or more conventional electrolyte solvents are mixed with the hydrofluoroolefin compound(s) (for example, such that the hydrofluoroolefin(s) constitute from about 1 to about 80 or 90 percent of the resulting solvent composition). Useful conventional electrolyte solvents include, for example, organic and fluorine-containing electrolyte solvents (for example, propylene carbonate, ethylene carbonate, dimethyl carbonate, diethyl carbonate, ethyl methyl carbonate, dimethoxyethane, 7-butyrolactone, diglyme (that is, diethylene glycol dimethyl ether), tetraglyme (that is, tetraethylene glycol dimethyl ether), monofluoroethylene carbonate, vinylene carbonate, ethyl acetate, methyl butyrate, tetrahydrofuran, alkyl-substituted tetrahydrofuran, 1,3-dioxolane, alkyl-substituted 1,3-dioxolane, tetrahydropyran, alkyl-substituted tetrahydropyran, and the like, and mixtures thereof). Other conventional electrolyte additives (for example, a surfactant) can also be present, if desired.

The present disclosure further relates to electrochemical cells (e.g., fuel cells, batteries, capacitors, electrochromic windows) that include the above-described electrolyte compositions. Such an electrochemical cell may include a positive electrode, a negative electrode, a separator, and the above-described electrolyte composition.

A variety of negative and positive electrodes may be employed in the electrochemical cells. Representative negative electrodes include graphitic carbons e.g., those having a spacing between (002) crystallographic planes, $d_{002}$, of 3.45 Å>$d_{002}$>3.354 Å and existing in forms such as powders, flakes, fibers or spheres (e.g., mesocarbon microbeads); $Li_{4/3}Ti_{5/3}O_4$ the lithium alloy compositions described in U.S. Pat. No. 6,203,944 (Turner '944) entitled "ELECTRODE FOR A LITHIUM BATTERY" and PCT Published Patent Application No. WO 00103444 (Turner PCT) entitled "ELECTRODE MATERIAL AND COMPOSITIONS"; and combinations thereof. Representative positive electrodes include $LiFePO_4$, $LiMnPO_4$, $LiCoPO_4$, $LiMn_2O_4$, $LiCoO_2$ and combinations thereof. The negative or positive electrode may contain additives such as will be familiar to those skilled in the art, e.g., carbon black for negative electrodes and carbon black, flake graphite and the like for positive electrodes.

The electrochemical devices of the present disclosure can be used in various electronic articles such as computers, power tools, automobiles, telecommunication devices, and the like.

Embodiments

1. A hydrofluoroolefin compound represented by the following general formula (I):

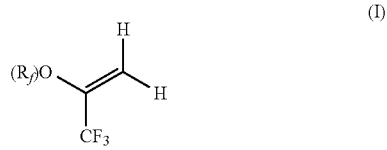

wherein $R_f$ is a linear or branched perfluorinated alkyl group containing 2-10 carbon atoms and optionally contains (i) at least one catenated heteroatom selected from O or N; or (ii) a ring structure having 3 to 6 ring carbon atoms that optionally contains one or more catenated heteroatoms selected from O or N.

2. The hydrofluoroolefin compound of embodiment 1, wherein $R_f$ contains 3-10 carbon atoms.
3. The hydrofluoroolefin compound according to any one of the preceding embodiments, wherein $R_f$ is linear.
4. The hydrofluoroolefin compound according to any one of the preceding embodiments, wherein $R_f$ is branched.
5. The hydrofluoroolefin compound according to any one of the preceding embodiments, wherein $R_f$ contains at least one catenated heteroatom selected from O or N.
6. A working fluid comprising a hydrofluoroolefin compound according to any one of the preceding embodiments, wherein the hydrofluoolefin compound is present in the working fluid at an amount of at least 25% by weight based on the total weight of the working fluid.
7. An apparatus for heat transfer comprising:
    a device; and
    a mechanism for transferring heat to or from the device, the mechanism comprising a heat transfer fluid that comprises a hydrofluoolefin compound or working fluid according to any one of embodiments 1-6.
8. An apparatus for heat transfer according to embodiment 7, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.
9. An apparatus for heat transfer according to any one of embodiments 7-8, wherein the mechanism for transferring heat is a component in a system for maintaining a temperature or temperature range of an electronic device.
10. A method of transferring heat comprising:
    providing a device; and
    transferring heat to or from the device using a heat transfer fluid that comprises a hydrofluoroolefin compound or working fluid according to any one of embodiments 1-6.
11. A fire extinguishing composition comprising:
    (a) a hydrofluoroolefin compound or working fluid according to any one of embodiments 1-6;
    (b) at least one co-extinguishing agent comprising one or more hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, and mixtures thereof,
    wherein (a) and (b) are present in an amount sufficient to suppress or extinguish a fire.
12. A fire extinguishing composition according to embodiment 11, wherein (a) and (b) are in a weight ratio of from about 9:1 to about 1:9.
13. A method of extinguishing a fire comprising:
    applying to the fire a fire extinguishing composition comprising a hydrofluoroolefin compound or working fluid according to any one of embodiments 1-6; and
    suppressing the fire.
14. A method of extinguishing a fire according to embodiment 11, wherein the fire extinguishing composition further comprises at least one co-extinguishing agent comprising one or more hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, and mixtures thereof.
15. An apparatus for converting thermal energy into mechanical energy in a Rankine cycle comprising:
    a working fluid;
    a heat source to vaporize the working fluid and form a vaporized working fluid;
    a turbine through which the vaporized working fluid is passed thereby converting thermal energy into mechanical energy;
    a condenser to cool the vaporized working fluid after it is passed through the turbine; and
    a pump to recirculate the working fluid,
    wherein the working fluid comprises a hydrofluoroolefin compound according to any one of embodiments 1-6.
16. A process for converting thermal energy into mechanical energy in a Rankine cycle comprising:
    vaporizing a working fluid with a heat source to form a vaporized working fluid;
    expanding the vaporized working fluid through a turbine;
    cooling the vaporized working fluid using a cooling source to form a condensed working fluid; and
    pumping the condensed working fluid;
    wherein the working fluid comprises a hydrofluoroolefin compound according to any one of embodiments 1-6.
17. A process for recovering waste heat comprising:
    passing a liquid working fluid through a heat exchanger in communication with a process that produces waste heat to produce a vaporized working fluid;
    removing the vaporized working fluid from the heat exchanger;
    passing the vaporized working fluid through an expander, wherein the waste heat is converted into mechanical energy; and
    cooling the vaporized working fluid after it has been passed through the expander;
    wherein the working fluid comprises a hydrofluoroolefin compound according to any one of embodiments 1-6.
18. A foamable composition comprising:
    a blowing agent;
    a foamable polymer or a precursor composition thereof; and
    a nucleating agent, wherein said nucleating agent comprises a hydrofluoroolefin compound or working fluid according to any one of embodiments 1-6.

19. A foamable composition according to embodiment 18, wherein the nucleating agent and the blowing agent are in a molar ratio of less than 1:2.

20. A foamable composition according to any one of embodiments 18-19, wherein the blowing agent comprises an aliphatic hydrocarbon having from about 5 to about 7 carbon atoms, a cycloaliphatic hydrocarbon having from about 5 to about 7 carbon atoms, a hydrocarbon ester, water, or combinations thereof.

21. A process for preparing polymeric foam comprising:
vaporizing at least one liquid or gaseous blowing agent or generating at least one gaseous blowing agent in the presence of at least one foamable polymer or a precursor composition thereof and a nucleating agent, wherein said nucleating agent comprises a hydrofluoroolefin compound or working fluid according to any one of embodiments 1-6.

22. A foam made with the foamable composition according to embodiment 19.

23. A device comprising:
a dielectric fluid comprising a hydrofluoroolefin compound or working fluid according to any one of embodiments 1-6;
wherein the device is an electrical device.

24. The device of embodiment 23, wherein said electrical device comprises a gas-insulated circuit breakers, current-interruption equipment, a gas-insulated transmission line, a gas-insulated transformers, or a gas-insulated substation.

25. The device according to any one of embodiments 23-24, wherein the dielectric fluid further comprises a second dielectric gas.

26. The device of embodiment 23, wherein the second dielectric gas comprises an inert gas.

27. The device of embodiment 26, wherein the second dielectric gas comprises nitrogen, helium, argon, or carbon dioxide.

28. A coating composition comprising:
a solvent composition comprising a hydrofluoroolefin compound or working fluid according to any one of embodiments 1-6; and
a coating material that is soluble or dispersible in said solvent composition.

29. The coating composition according to embodiment 28, wherein said coating material comprises a pigment, lubricant, stabilizer, adhesive, anti-oxidant, dye, polymer, pharmaceutical, release agent, inorganic oxide.

30. The composition according to embodiment 28, wherein said coating material comprises a perfluoropolyether, a hydrocarbon, a silicone lubricant, a copolymer of tetrafluoroethylene, or a polytetrafluoroethylene.

31. A cleaning composition comprising:
a hydrofluoroolefin compound or working fluid according to any one of embodiments 1-6; and
a co-solvent.

32. The composition of embodiment 31, wherein said hydrofluoroolefin compound or working fluid is greater than 50 percent by weight of said composition based on the total weights of the fluorinated olefin compound and the co-solvent.

33. The composition according to any one of embodiments 31-32, wherein said co-solvent comprises alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof.

34. A cleaning composition comprising:
a hydrofluoroolefin compound or working fluid according to any one of embodiments 1-6; and
a surfactant.

35. The composition of embodiment 34, wherein the cleaning composition comprises from 0.1 to 5 percent by weight surfactant.

36. The composition according to any one of embodiments 34-35, wherein the surfactant comprises a nonionic surfactant comprising an ethoxylated alcohol, an ethoxylated alkylphenol, an ethoxylated fatty acid, an alkylaryl sulfonate, a glycerolester, an ethoxylated fluoroalcohol, a fluorinated sulfonamide, or mixtures thereof.

37. A process for removing contaminants from a substrate, the process comprising the steps of:
contacting a substrate with a composition comprising:
a hydrofluoroolefin compound or working fluid according to any one of embodiments 1-6; and
a co-solvent.

38. An electrolyte composition comprising:
a solvent composition comprising at least one hydrofluoroolefin compound or working fluid according to any one of embodiments 1-6; and
an electrolyte salt.

39. A process for manufacturing a hydrofluoroolefin compound or working fluid according to any one of embodiments 1-6, the process comprising reduction of a perfluorinated vinyl or propenyl amine with a reducing agent capable of replacing one or more F atoms of the perfluorinated vinyl or propenyl group with H.

40. The process according to embodiment 39, wherein the reducing agent is a hydride reducing agent.

The operation of the present disclosure will be further described with regard to the following detailed examples. These examples are offered to further illustrate various embodiments and techniques. It should be understood, however, that many variations and modifications may be made while remaining within the scope of the present disclosure.

EXAMPLES

Compositions of the present disclosure were prepared and analyzed as described below. Unless otherwise indicated, all parts and percentages are by weight. Unless otherwise indicated, all materials were obtained from Sigma-Aldrich Company, St. Louis, Mo., USA.

| List of Materials | | |
|---|---|---|
| Material | Description | Source |
| Tetraglyme | Tetraethylene glycol dimethyl ether | Alfa Aesar, US |
| $NaBH_4$ | Sodium borohydride | Alfa Aesar, US |
| Methanol | | Sigma-Aldrich, US |
| $TiCl_4$ | Titanium(IV) chloride | Sigma-Aldrich, US |
| Zn dust | Zinc dust | Fisher Scientific, US |
| THF | Tetrahydrofuran | Sigma-Aldrich, US |

Example 1

Preparation of 3,3,3-trifluoro-2-(1,1,2,2,3,3,-hexafluoro-3-(trifluoromethoxy)propoxy)prop-1-ene

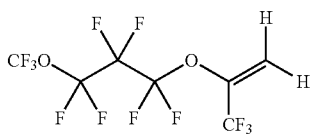

To a 3-neck flask equipped with a temperature probe, magnetic stir bar, water-cooled condenser, and addition funnel was charged sodium borohydride (12.0 g, 317 mmol) and tetrahydrofuran (100 mL). 2,3,3,3-Tetrafluoro-2-(1,1,2,2,3,3-hexafluoro-3-(trifluoromethoxy)propoxy)propanoyl fluoride (60.0 g, 151 mmol) was added dropwise to the resultant mixture. After complete addition, the reaction mixture was heated to reflux and stirred overnight. The mixture was then allowed to cool to room temperature followed by the dropwise addition of methanol (80 mL) and H$_2$O (50 mL). The mixture was then transferred to a separatory funnel and the fluorous phase was collected and then distilled to afford 2,3,3,3-tetrafluoro-2-(1,1,2,2,3,3-hexafluoro-3-(trifluoromethoxy)propan-1-ol (33 g, 58%) as a colorless liquid. The isolated compound was used in the next step.

To a 3-neck flask equipped with a temperature probe, distillation head, overhead stirrer, and under N2 was charged TiCl$_4$ (6.4 mL, 58 mmol). 2,3,3,3-Tetrafluoro-2-(1,1,2,2,3,3-hexafluoro-3-(trifluoromethoxy)propan-1-ol (14.9 g, 39.0 mmol) was added dropwise with stirring and the resultant mixture was heated to 40° C. followed by a 30 min stir. The mixture was then cooled to 0° C. followed by the dropwise addition of tetraethylene glycol dimethyl ether (50 mL). Exotherms reaching approximately 20° C. were observed. The resultant mixture was allowed to warm to room temperature followed by the addition of zinc dust (7.9 g, 120 mmol) in one portion. The resultant reaction mixture was raised to 85° C. After a 3 h stir, the temperature was slowly raised to 185° C. and distillate was collected with the distillation head temperature reaching 83° C. affording the title compound (5.6 g, 41%) as a colorless liquid.

Example 2

Preparation of 3,3,3-trifluoro-2-(perfluoropropoxy)prop-1-ene

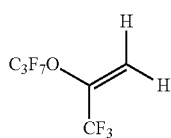

To a 3-neck flask equipped with a temperature probe, magnetic stir bar, water-cooled condenser, and addition funnel was charged sodium borohydride (16.0 g, 423 mmol), and tetraethylene glycol dimethyl ether (125 mL). 2,3,3,3-Tetrafluoro-2-(1,1,2,2,3,3,3-heptafluoropropoxy)propanoyl fluoride (100 g, 301 mmol) was added dropwise to the resultant mixture. After complete addition, the reaction mixture was heated to reflux and stirred overnight. The mixture was then allowed to cool to room temperature followed by the dropwise addition of methanol (100 mL) and H$_2$O (150 mL). The mixture was then transferred to a separatory funnel and the fluorous phase was collected and then distilled (46.1° C., 40 torr) to afford 2,3,3,3-tetrafluoro-2-(1,1,2,2,3,3-heptafluoropropoxy)propan-1-ol (67.5 g, 71%) as a colorless liquid. The isolated compound was used in the next step.

To a 3-neck flask equipped with a temperature probe, distillation head, overhead stirrer, and under N2 was charged TiCl$_4$ (7.9 mL, 72 mmol). 2,3,3,3-Tetrafluoro-2-(1,1,2,2,3,3-heptafluoropropoxy)propan-1-ol (15.1 g, 47.8 mmol) was added dropwise with stirring and the resultant mixture was heated to 40° C. followed by a 30 min stir. The mixture was then allowed to cool to room temperature followed by the dropwise addition of tetraethylene glycol dimethyl ether (45 mL). Exotherms reaching approximately 50° C. were observed. The resultant mixture was allowed to warm to room temperature followed by the addition of zinc dust (9.1 g, 140 mmol) in one portion. The resultant reaction mixture was raised to 85° C. After a 3 h stir, the temperature was slowly raised to 225° C. and distillate was collected with the distillation head temperature reaching 69° C. affording the title compound (4.1 g, 31%) as a colorless liquid.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows. All references cited in this disclosure are herein incorporated by reference in their entirety.

What is claimed is:

1. A hydrofluoroolefin compound represented by the following general formula (I):

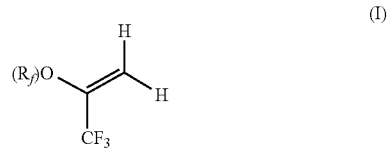

wherein R$_f$ is a linear or branched perfluorinated alkyl group containing 2-10 carbon atoms and optionally contains: (i) at least one catenated heteroatom selected from O or N; or (ii) a ring structure having 3 to 6 ring carbon atoms that optionally contains one or more catentated heteroatoms selected from O or N.

2. The hydrofluoroolefin compound of claim 1, wherein R$_f$ contains 3-10 carbon atoms.

3. The hydrofluoroolefin compound according to claim 1, wherein R$_f$ is linear.

4. The hydrofluoroolefin compound according to claim 1, wherein R$_f$ is branched.

5. The hydrofluoroolefin compound according to claim 1, wherein R$_f$ contains at least one catenated heteroatom selected from O or N.

6. A working fluid comprising hydrofluoroolefin compound according to claim 1, wherein the hydrofluroolefin compound is present in the working fluid at an amount of at least 25% by weight based on the total weight of the working fluid.

7. An apparatus for heat transfer comprising:
   a device; and
   a mechanism for transferring heat to or from the device, the mechanism comprising a heat transfer fluid that comprises the working fluid according to claim 6.

8. The apparatus for heat transfer according to claim 7, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

9. The apparatus for heat transfer according to claim 8, wherein the mechanism for transferring heat is a component in a system for maintaining a temperature or temperature range of an electronic device.

10. A method of transferring heat comprising:
    providing a device; and
    transferring heat to or from the device using a heat transfer fluid that comprises the working fluid according to claim 6.

* * * * *

UNITED STATES PATENT AND TRADEMARK OFFICE
CERTIFICATE OF CORRECTION

| | |
|---|---|
| PATENT NO. | : 10,717,694 B2 |
| APPLICATION NO. | : 16/099719 |
| DATED | : July 21, 2020 |
| INVENTOR(S) | : Sean Michael Smith |

It is certified that error appears in the above-identified patent and that said Letters Patent is hereby corrected as shown below:

On the Title Page

<u>Column 2 – Page 2</u>
Line 3, Delete "Stregth:" and insert -- Strength: --, therefor.
Line 6, Delete "1,2-difloroethylenes"," and insert -- 1,2-difluoroethylenes", --, therefor.
Line 9, Delete "ocoboltate(III)" and insert -- cobaltate(III) --, therefor.
Line 7, Delete "catentated" and insert -- catenated --, therefor.
Line 11, Delete "N-Chlorobistrufluoromethylamine" and insert
-- N-Chlorobistrifluoromethylamine --, therefor.
Line 17, Delete "1,2-Di(bistrifluromethylamino)-" and insert -- 1,2-Di(bistrifluoromethylamino)- --, therefor.
Line 26, Delete "polyuorovinylamines" and insert -- polyfluorovinylamines --, therefor.

In the Specification

<u>Column 1</u>
Line 49, Delete "catentated" and insert -- catenated --, therefor.
Line 53, Delete "hydrofluoolefin" and insert -- hydrofluoroolefin --, therefor.
Line 61, Delete "hydrofluoolefin" and insert -- hydrofluoroolefin --, therefor.

<u>Column 3</u>
Line 19, Delete "catentated" and insert -- catenated --, therefor.
Line 22-23, Delete "catentated" and insert -- catenated --, therefor.

<u>Column 6</u>
Line 9, Delete "perfluorintated" and insert -- perfluorinated --, therefor.
Line 13, Delete "catentated" and insert -- catenated --, therefor.

Signed and Sealed this
Twenty-fourth Day of October, 2023

Katherine Kelly Vidal
*Director of the United States Patent and Trademark Office*

CERTIFICATE OF CORRECTION (continued)
U.S. Pat. No. 10,717,694 B2

Column 13
Line 47-54, Delete "For example, coating materials may include perfluoropolyether, hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, perfluoropolyethers, polysiloxanes, stearic acid, acrylic adhesives, polytetrafluoroethylene, amorphous copolymers of tetrafluoroethylene, or combinations thereof." and insert the same on Column 13, Line 46 as a continuation of the same paragraph.

Column 15
Line 6, Delete "alkylarysulfonates," and insert -- alkylarylsulfonates, --, therefor.

Column 19
Line 19, Delete "catentated" and insert -- catenated --, therefor.
Line 32, Delete "hydrofluoolefin" and insert -- hydrofluoroolefin --, therefor.
Line 39, Delete "hydrofluoolefin" and insert -- hydrofluoroolefin --, therefor.

Column 22
Line 17, Delete "glycerolester," and insert -- glycerol ester, --, therefor.

In the Claims

Column 24
Line 56, In Claim 1, delete "catentated" and insert -- catenated --, therefor.
Line 66, In Claim 6, after "comprising" insert -- the --.
Line 67, In Claim 6, delete "hydrofluroolefin" and insert -- hydrofluoroolefin --, therefor.